(12) United States Patent
Matthison-Hansen (10) Patent No.: US 11,690,502 B2
(45) Date of Patent: Jul. 4, 2023

(54) ENDOSCOPE

(71) Applicant: AMBU A/S, Ballerup (DK)

(72) Inventor: Kaspar Mat Matthison-Hansen, Helsingør (DK)

(73) Assignee: AMBU A/S, Ballerup (DK)

( * ) Notice: Subject to any disclaimer, the term of this patent is extended or adjusted under 35 U.S.C. 154(b) by 453 days.

(21) Appl. No.: 16/833,506

(22) Filed: Mar. 27, 2020

(65) Prior Publication Data

US 2020/0221927 A1  Jul. 16, 2020

Related U.S. Application Data

(63) Continuation-in-part of application No. PCT/DK2018/050238, filed on Sep. 27, 2018.

(30) Foreign Application Priority Data

Sep. 28, 2017 (DK) .......................... PA 2017 70734

(51) Int. Cl.
*A61B 1/00* (2006.01)
*A61B 1/005* (2006.01)
*A61B 1/04* (2006.01)

(52) U.S. Cl.
CPC .......... *A61B 1/0051* (2013.01); *A61B 1/0052* (2013.01); *A61B 1/00066* (2013.01); *A61B 1/00087* (2013.01); *A61B 1/00154* (2013.01); *A61B 1/04* (2013.01); *A61B 1/042* (2013.01)

(58) Field of Classification Search
None
See application file for complete search history.

(56) References Cited

U.S. PATENT DOCUMENTS

| 4,624,243 A * | 11/1986 | Lowery .............. A61B 1/00165 600/114 |
| 5,535,759 A | 7/1996 | Wilk |
| 5,611,769 A | 3/1997 | Monroe |
| 5,908,381 A | 6/1999 | Aznoian et al. |

(Continued)

FOREIGN PATENT DOCUMENTS

| DE | 4223897 A1 | 1/1994 |
| EP | 2130479 A1 | 12/2009 |

(Continued)

OTHER PUBLICATIONS

Examination Report issued in EP18782301.8, dated Jan. 9, 2023, 5 pages.

(Continued)

*Primary Examiner* — Timothy J Neal
(74) *Attorney, Agent, or Firm* — Faegre Drinker Biddle & Reath LLP (57) ABSTRACT

An endoscope (1) including a handle (2) arranged at a proximal end and an insertion tube (3) extending from said handle (2) towards a distal end, a bending section (7) arranged at the distal end and controllable by and operator via control input means (8) arranged at the handle (2); and at least one insertion tube part with at least one lumen, wherein the bending section (7) is displaceable in said lumen so as to be movable relative to the insertion tube (3) from a retracted position within said lumen to an extended position at least partially outside said lumen.

20 Claims, 8 Drawing Sheets

(56) References Cited

U.S. PATENT DOCUMENTS

| | | | |
|---|---|---|---|
| 6,419,654 B1* | 7/2002 | Kadan | A61M 1/774 600/101 |
| 6,605,036 B1 | 8/2003 | Wild | |
| 6,749,560 B1* | 6/2004 | Konstorum | A61B 1/00071 604/525 |
| 6,761,684 B1 | 7/2004 | Speier | |
| 8,012,083 B2* | 9/2011 | Kucklick | A61B 17/00234 600/128 |
| 9,011,429 B2* | 4/2015 | Mitchell | A61B 17/320016 606/1 |
| 9,179,831 B2 | 11/2015 | McGrail et al. | |
| 9,220,400 B2 | 12/2015 | Petersen | |
| 9,854,962 B2 | 1/2018 | McGrail et al. | |
| 10,321,804 B2 | 6/2019 | Jacobsen et al. | |
| 10,406,309 B2 | 9/2019 | Daher | |
| 10,478,054 B2 | 11/2019 | Nave et al. | |
| 2005/0192532 A1 | 9/2005 | Kucklick et al. | |
| 2005/0272975 A1 | 12/2005 | McWeeney | |
| 2007/0225562 A1 | 9/2007 | Spivey et al. | |
| 2007/0249899 A1* | 10/2007 | Seifert | A61B 1/0004 600/176 |
| 2008/0167527 A1 | 7/2008 | Slenker et al. | |
| 2009/0054728 A1 | 2/2009 | Trusty | |
| 2011/0301093 A1* | 12/2011 | Kimchi | G01N 33/6872 435/235.1 |
| 2015/0289754 A1 | 10/2015 | Bendory et al. | |
| 2017/0055813 A1 | 3/2017 | Brown et al. | |
| 2018/0296068 A1 | 10/2018 | Matthison-Hansen et al. | |
| 2018/0303315 A1 | 10/2018 | Matthison-Hansen | |
| 2018/0303316 A1 | 10/2018 | Matthison-Hansen | |
| 2018/0303317 A1 | 10/2018 | Matthison-Hansen | |
| 2019/0216294 A1 | 7/2019 | Matthison-Hansen | |

FOREIGN PATENT DOCUMENTS

| | | |
|---|---|---|
| WO | 2000054653 A1 | 9/2000 |
| WO | 2007109418 A2 | 9/2007 |
| WO | 2007146987 A2 | 12/2007 |
| WO | 2013101998 A1 | 7/2013 |
| WO | 2014072977 A1 | 5/2014 |
| WO | 2015061756 A1 | 4/2015 |
| WO | 2017015480 A1 | 1/2017 |

OTHER PUBLICATIONS

First Office Action issued in CN201880055976.5, dated Jan. 10, 2023, 14 pages (8 pages of English translation and 6 pages of original documents), Jan. 10, 2023.

Examination report in Danish application No. PA 2017 70734 dated Mar. 23, 2018, 6 pages.

ISR and Written Opinion in International Application No. PCT/DK2018/050238, dated Dec. 19, 2018, 10 pages.

Gidea, Thomas, et al., "Electromagnetic Navigation Diagnostic Bronchoscopy, A Prospective Study," Am J Respir Crit Care Med vol. 174. pp 982-989, Jul. 27, 2006, 8 pages.

Yeung, Baldwin Po Man, "A technical review of flexible endoscopic multitasking platforms," International Journal of Surgery, May 26, 2012, Surgical Associates Ltd. Published by Elsevier Ltd., 10 pages.

* cited by examiner

ENDOSCOPE

CROSS-REFERENCE TO RELATED APPLICATIONS

The present application is a continuation-in-part of International Application No. PCT/DK2018/050238, filed Sep. 27, 2018, which claims the benefit of Danish Patent Application No. PA 2017 70734, filed Sep. 28, 2017, which applications are incorporated by reference herein in their entirety.

FIELD OF THE DISCLOSURE

The present invention relates to an endoscope. More specifically, the present invention relates to an endoscope comprising a handle arranged at a proximal end, an insertion tube extending from said handle towards a distal end, a controllable bending section arranged at the distal end, said controllable bending section being controllable by and operator via control input means arranged at the handle.

BACKGROUND OF THE DISCLOSURE

In general, an endoscope comprises an operating handle at the proximal end and an insertion tube extending from the handle towards the distal end. The handle is adapted to be held by an operator and inter alia comprises externally protruding operating members connected to internal control means allowing the operator to control the movement of a controllable bending section at the distal end of the insertion tube, while advancing the distal end of the insertion tube to a desired location e.g. within a body cavity of a person. By means of an attached monitoring device, such as a monitor with a display screen, the location to which the distal end has been advanced may be inspected using the endoscope. The term "videoscope" may be used more generally to refer to a device including the parts described above but used in a variety of medical procedures including endoscopy, arthroscopy, and other minimally invasive procedures. Unless otherwise stated, in the present application the parts, features, and functions described with reference to an endoscope are equally applicable to a videoscope. Medical videoscopes comprise endoscopes, colonoscopes, ear-nose-throat scopes, duodenoscopes, and any other medical device having a handle, an image sensor configured to obtain images of views of a patient, and an insertion portion between the handle and the image sensor. The term "patient" herein includes humans and animals. Portable medical monitors can be communicatively coupled to the medical videoscopes to receive image data therefrom and present images corresponding to the image data on a display module of the monitor.

Often, however, inspection is not all that is desired, e.g. where the inspection is to locate the site for further actions. An example of one such situation where other action than inspection is desired is bronchoalveolar lavage or BAL. BAL is a commonly used procedure for obtaining samples of organic material from a lung segment of a patient. This is basically done by flushing a lung segment with sterile water and then sucking the water into a sample container. More specifically the distal end of an endoscope is advanced to the location in the lung from where the sample is to be taken. The distal end of the insertion tube is then pressed into firm engagement against the interior of the lung to help securing the position in a process commonly referred to as wedging. Via the working channel of the endoscope, sterile water, e.g. a 0.9% saline solution, is then instilled into the lung at the sample location and as much as possible extracted again, now containing organic material, and thus constituting a sample. How deep the distal end of the insertion tube can be advanced into the alveoles is limited by the external dimensions of the distal tip of the insertion tube, i.e. the diameter thereof as the insertion tube is normally circular in cross-section.

Also in other situations, the external dimensions of the insertion tube limit the versatility of the endoscope, more specifically the minimum bending radius of the bending section of the endoscope. The controllable bending section is normally an articulated section at the distal tip of the insertion tube that can be controlled by the operator from the handle, allowing the operator to advance the distal tip of the endoscope to a desired location by means of a series of actions involving inter alia bending the bending section in a desired direction, advancing the insertion tube and turning the insertion tube by turning the handle which is rigidly connected thereto. Having negotiated a tortuous path of bends and turns to a location of interest, there may still be very limited space to bend the bending section towards the target of interest. This is e.g. the case if the endoscope is to be used to inspect the biliary duct from the duodenum, because the narrow biliary duct terminates almost perpendicular into the side wall of the duodenum.

In respect of the external dimensions of the insertion tube, US2017/0055813 discloses a medical introducer with an introducer tube with several lumens. One of the lumens may accommodate a steerable working channel member controlled by a control knob on a handle at the proximal end of the introducer tube. The control knob may be displaced with respect to the handle of the introducer tube in order to move the steerable working channel member, e.g. to advance the bending section beyond the distal end of the introducer tube.

SUMMARY

On this background the present invention sets out to provide an easy to use endoscope with a reduced bending radius of the distal tip of the endoscope and a high degree of flexibility and precision.

According to a first aspect of the disclosure this object is achieved by an endoscope comprising a handle arranged at a proximal end, an insertion tube extending from said handle towards a distal end, a controllable bending section arranged at the distal end, said controllable bending section being controllable by an operator via control input means arranged at the handle, wherein the insertion tube comprises at least one insertion tube part with at least one lumen and wherein the bending section is displaceable in said lumen so as to be movable relative to the insertion tube part from a retracted position within said lumen to an extended position at least partially outside said lumen, and wherein the controllable bending section is located at a fixed distance from the handle, and the at least one insertion tube part is adapted for a reciprocating movement with respect to the handle.

With this arrangement the controllable bending section may be provided with a substantially narrower cross-wise dimension, i.e. diameter, than the insertion tube in general. In turn this means that when the controllable bending section is advanced out of the insertion tube, i.e. out of the distal end of the at least one insertion tube part, it is no longer restricted by the insertion tube as such, in particular the diameter and the rigidity thereof, but may bend to a much smaller radius. At the same time the relative movement of the bending section with respect to the insertion tube does not influence the control of the bending section, because the force transmission means such as Bowden cables from the handle to the controllable bending section reciprocate in unison with the handle including the operating means and the bending section.

According to a preferred embodiment of the first aspect of the disclosure, the at least one insertion tube part is adapted for a releasable locking engagement with respect to the handle. Thereby, the insertion tube can be kept as an integral piece of the endoscope, allowing the endoscope to function in a conventional manner for most of a procedure such as insertion to the target location. Only then can the at least one insertion tube part be released, and be slid away from the articulated bending section, so as to utilize the then increased bending capabilities of the articulated bending section.

According to a further preferred embodiment, the controllable bending section comprises a number of articulated parts. Such a controllable bending section has a high degree of flexibility and is easy to manufacture using existing technology, e.g. as disclosed in WO2016/188543 or WO2014/106511, both incorporated herein by reference.

According to a further preferred embodiment according to the first aspect of the disclosure, the at least one insertion tube part comprises a vision device, such as a camera. Not having to incorporate the vision device in the tip of the articulated bending section, but in the at least one insertion tube part in which the articulated bending section may reciprocate in and out, allows the articulated bending section to be made with even smaller cross-sectional dimensions. This is in particular the case if the flexible bending section also does not incorporate a working channel, e.g. because any working channel is in or within the at least one insertion tube part.

However, it is in a further embodiment according to the first aspect of the disclosure preferred that the controllable bending section comprises a working channel, such as a suction channel. That is to say, the working channel is adapted to be connectable to a suction means, i.e. an external vacuum source. This allows liquid, mucus or the like to be removed from a desired location through the endoscope, in turn allowing the endoscope to be used for the aforesaid bronchoalveolar lavage procedure. For other procedures, the controllable bending section may preferably comprise a tool, e.g. a simple tool such as a needle, in particular a biopsy needle.

DESCRIPTION OF THE DRAWINGS

The invention will now be described in greater detail based on non-limiting exemplary embodiments and with reference to the drawings, on which.

DETAILED DESCRIPTION OF DISCLOSED EMBODIMENTS

Figure 1:
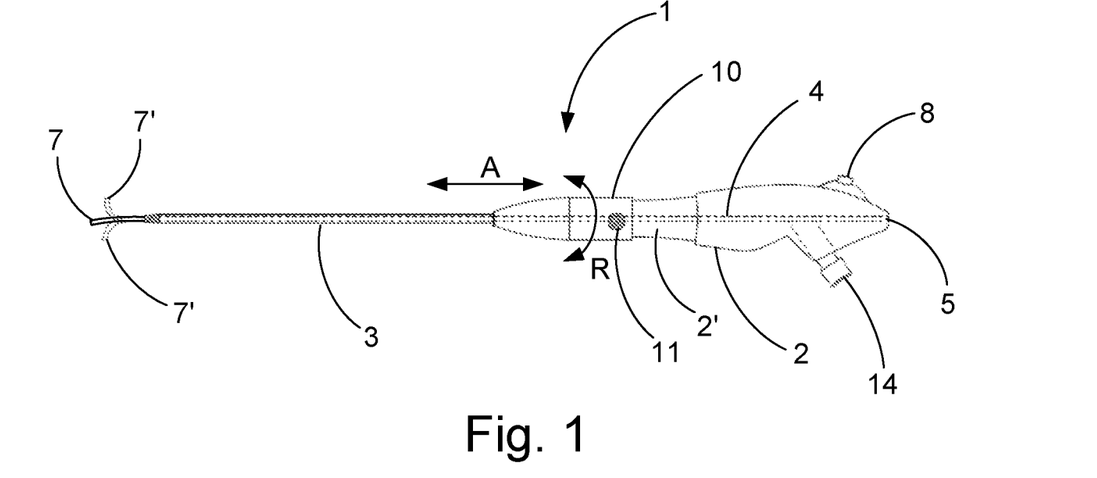
FIG. 1 is a side view of an embodiment of an endoscope according to the present disclosure.

Turning first to FIG. 1, an endoscope 1 is shown in side view. From an endoscope handle 2 at the proximal end of the endoscope 1 an insertion tube 3 extends towards the distal end of the endoscope 1. For illustration purposes some of the internal features of the endoscope 1 are shown in broken lines. These include a working channel 4 having an entry port 5 at the proximal end of the endoscope handle 2 and an exit port 6 at the distal end of an articulated bending section 7 at the distal end of the endoscope 1. Using an operating member 8, such as a knob on the endoscope handle 2 the bending of the articulated bending section 7 may be controlled, e.g. deflected sideways to positions 7' also illustrated in broken lines. The control of the articulated bending section 7 by means of the operating member 8 takes place via control members known per se, such as Bowden cables or the like connected to the operating member and the most distal segment 9 of the articulated bending section 7, as generally explained in the aforementioned disclosures WO2016/188543 and WO2014/106511. It should be noted, however, that providing the controllable bending section as an articulated bending section is only a preferred embodiment, and that other ways of providing the controllable bending section may be envisaged.

However, unlike the endoscopes described in WO2016/188543 and WO2014/106511, the articulated bending section 7 is not contiguous with the insertion tube 3. Instead, the articulated bending section 7 has a much smaller diameter than the insertion tube 3 and is accommodated in a displaceable manner in a suitable channel or lumen in or within the insertion tube 3, through which also a more rigid non-controllable part extends (see insertion shaft 23 in FIGS. 3, 4, and 10-12). The insertion shaft interconnects the endoscope handle 2 with the articulated bending section 7, allowing insertion tube 3 to slide or translate longitudinally relative to all three parts. The insertion shaft may be attached to the handle 2 and the bending section 7 in the same way a prior art insertion tube interconnects the handle 2 with the bending section 7.

Figure 2:
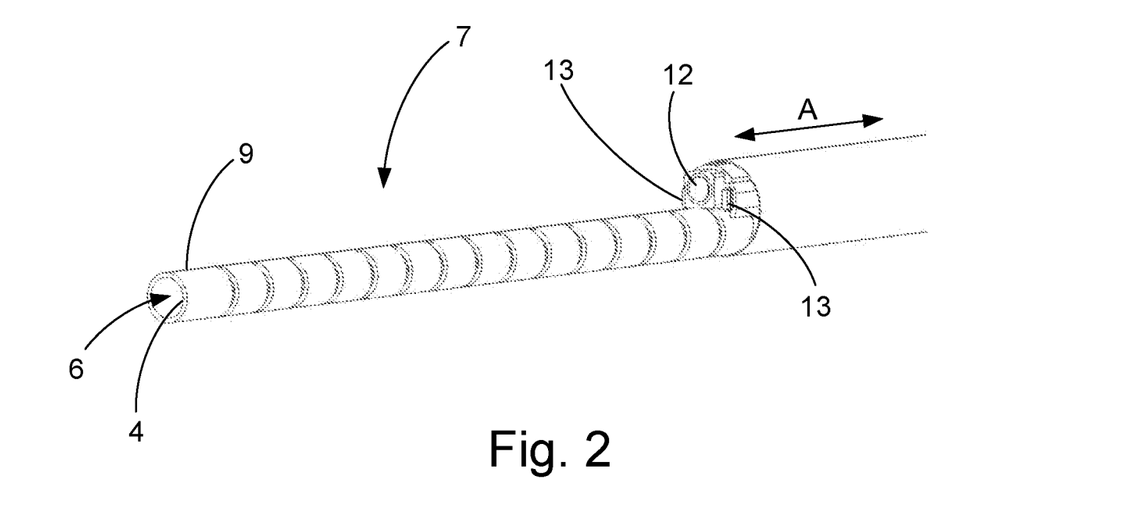
FIG. 2 is a detail view in perspective of the embodiment of the distal tip of the endoscope of FIG. 1.
Figure 3:
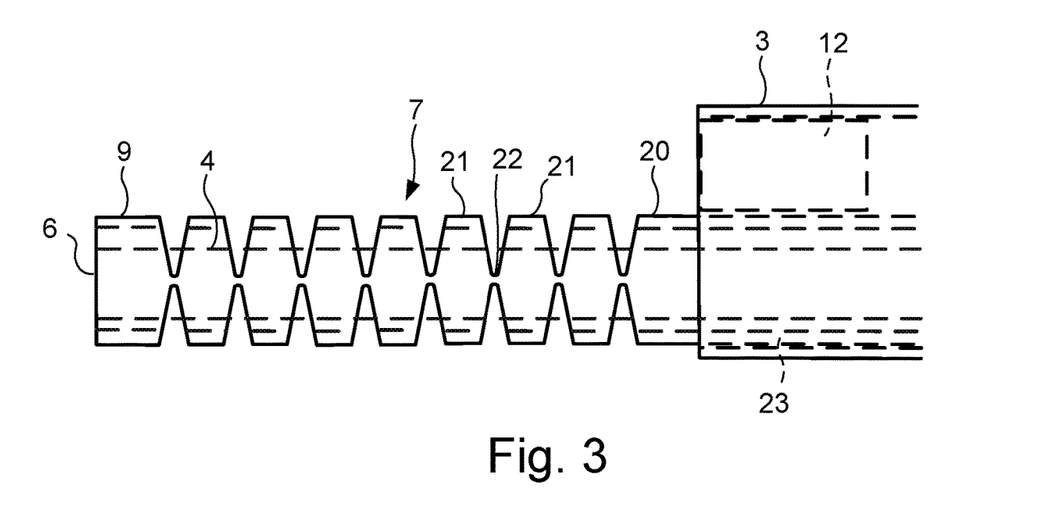
FIG. 3 is a schematic depiction of a bending section and an insertion tube in a retracted position.
Figure 4:
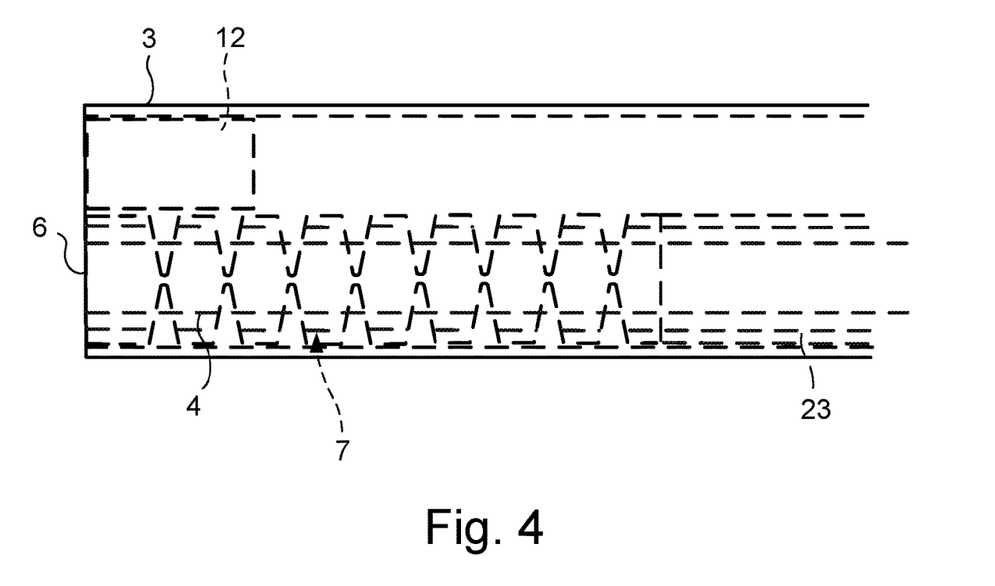
FIG. 4 is a schematic depiction of the bending section and the insertion tube in an extended position.

To effect this relative sliding motion, indicated with the double arrow A in FIGS. 1 and 2, the endoscope preferably comprises an auxiliary handle 10 rigidly connected to the insertion tube 3, preferably at the proximal end thereof. Being rigidly connected to the insertion tube 3, the auxiliary handle may be moved relatively to the handle 2 of the endoscope 1 and accordingly also relatively to the bending section 7. This allows the bending section 7 to be moved (relative to the insertion tube 3) from a position in the channel or lumen within the insertion tube 3, as shown in FIG. 4, to an advanced position, as shown in FIGS. 1-3, where the bending section 7 extends from the distal end of the insertion tube 3. When the bending section 7 is in the insertion tube 3, the insertion tube 3 is said to be in the locked position, shown in FIG. 11. When the bending section extends distally from the insertion tube 3, the insertion tube 3 is said to be in the retracted position, as shown in FIG. 12.

Preferably, the endoscope 1 comprises a releasable locking means for keeping the auxiliary handle 10 locked in position with respect to a handle extension 2' of the endoscope handle 2. The handle extension 2' and the auxiliary handle 10 are coextensive. An example of releasable locking means includes a push-button 11. Additional details of an example releasable locking means including push-button 11 is described with reference to FIGS. 10-12. Only when the push-button 11 is released is it possible to effect the relative sliding motion between the auxiliary handle 10 and the handle 2 of the endoscope 1 (and the insertion tube 3 and the bending section 7). It may be of advantage if, upon release of the releasable locking means, the auxiliary handle 10 may also turn relatively to the endoscope handle 2 as indicated by the arrow R in FIG. 1, thus allowing the bending section 7 to turn with respect to the insertion tube 3, in particular in front of the distal end thereof. Examples of rotated auxiliary handles/insertion tubes are depicted in FIGS. 6-9. Another example of releasable locking means includes bayonet coupling, where the auxiliary handle has a longitudinal slot with an offset aperture at the distal end and the handle has a radially extending protrusion or pin. The pin fits in the offset aperture and the slot. When the insertion tube is extended, as in FIG. 4, the offset aperture is mated with the pin in the locked position. Rotating the auxiliary handle by the offset amount allows the pin to move from the aperture to the slot, and then the auxiliary handle can be moved proximally as the pin slides in the slot. Another example of releasable locking means includes a friction fit. The handle portion entering the auxiliary handle, and the auxiliary handle, can be shaped so that rotation of the auxiliary handle creates friction and locks the insertion tube. For example, the handle portion entering the auxiliary handle can have an external slightly oval cross-section. The auxiliary handle can have an internal slightly oval cross-section. Rotation causes misalignment of the oval cross-sections increasing friction.

The insertion tube 3, surrounding the bending section 7 when the bending section 7 is in the retracted position inside the insertion tube 3, is provided with suitably thin walls and is made of a highly flexible material. That is to say, the inventor has realized that the insertion tube 3 may be so devised that even with a substantially reduced diameter of the bending section it will still be possible to provide sufficient forces to bend the retracted bending section 7 and thus the distal end of the insertion tube 3. Consequently, as long as the auxiliary handle 10 is in the locked (extended from the handle 2) position and the bending section 7 is inside the distal end of the insertion tube 3, the endoscope 1 may be maneuvered in an entirely conventional manner familiar to the operator. That is to say, by means of a series of steps involving selectively bending the bending section 7 using the operating member 8, and turning and advancing the endoscope 1 using the handle 2, the distal tip of the endoscope 1 may be maneuvered to a target location, e.g. a body cavity of a person such as a lung. The operator may visually follow his maneuvers on a monitor (not shown) communicatively connected to the endoscope 1 using live images captured by a vision device, such as preferably a camera 12, built into the tip of the endoscope 1 at the distal end of the insertion tube 3, the necessary illumination for the camera 12 being provided by one or more light sources such as LEDs 13. Though a camera 12 is preferred as the vision device, the skilled person will realize that this is only one option among others. The vision device could also be a light guide in the distal tip, leading the light to a remote camera or image sensor.

It should be noted that in practice the camera 12, LEDs 13 will be encapsulated, typically molded in, so as not to present any sharp edges or the like. The encapsulation has however been omitted in FIG. 2 for illustration purposes. This encapsulation or molding in, as such, is well known and one process for doing so is found in WO2010/066790, incorporated herein by reference, and further explained in WO2014/106511.

At the target location, however, the fact that the bond between the bending section 7 and the surrounding insertion tube 3 may be released by means of the releasable locking means, provides at least two advantages, in turn, opening new procedural possibilities. One, the bending section 7 may be advanced further into narrow cavities, not accessible by the insertion tube 3 as such, because of the larger diameter thereof. Two, by having a smaller diameter than the insertion tube 3 as such, the bending section 7 may be bent to a narrower radius than the insertion tube 3 once the bending section 7 has been advanced in front of the insertion tube 3, in turn, allowing sideways operations in narrow spaces not otherwise possible with an endoscope with a corresponding predetermined diameter of the insertion tube.

One of the possibilities the first advantage opens relates to BAL procedures where narrower cavities in the alveoli will be accessible.

Bronchoalveolar lavage or BAL is a commonly used procedure for obtaining samples of organic material from a lung segment of a patient. This is basically done by flushing a lung segment with sterile water and then sucking the water into a sample container. More specifically the distal end of the endoscope 1 is advanced to the location in the lung where the sample is to be taken. The distal end is then pressed into firm engagement against the interior of the lung to help securing the position in a process commonly referred to as wedging.

Via the working channel 4 of the endoscope 1, sterile water, e.g. a 0.9% saline solution, is instilled into the lung at the sample location and as much as possible extracted again, now containing organic material, and thus constituting a sample. Typically this is done by attaching a filled syringe of a volume between 20 ml and 60 ml, e.g. 50 ml to the working channel 5 of the endoscope 1, via a communication port in endoscope handle 2. The syringe is then used for each insertion as well as the subsequent extraction. This process is normally repeated several times in a row with new syringes, e.g. three to four, the samples being suitable for various purposes, depending on which number of sample in the sequence they are, because the composition of the organic material varies. Upon extraction they are therefore normally labelled accordingly. As an alternative to the extraction using the syringe, the extraction may be performed using an external suction and a Lukens trap.

This procedure involves at least two persons (e.g. and operator and an assistant) and quite a lot of preparation. The operator would normally be the doctor in charge of and responsible for the procedure, whereas the assistant would be a nurse. The operator would advance the tip of the endoscope 1 to the desired position, wedge it into position, and decide when to inject the sterile saline solution and when to extract the sample. The assistant would attach and remove the syringes, replace the Luken traps if external suction is used, label the samples, and under circumstances also operate the syringe and suction at the command of the operator, who decides the correct moment of injection and extraction. If external suction is used, the operator would himself activate a suction button 14 on the endoscope handle 2 using the one hand already in use for gripping the endoscope handle 2.

The procedure described above will be perfectly possible with the endoscope 1 according to the present invention, even with the bending section 7 locked inside the insertion tube 3.

However, as will be understood, the endoscope 1 allows for the instillation and suction deeper within the alveoli than conventional ones by advancing the narrower, articulated bending section 7 at least partially beyond the distal end of the insertion tube 3. More specifically, once the insertion tube 3 has been wedged in position, the operator may with the other hand, i.e. the hand not gripping the endoscope handle 2, grip the auxiliary handle 10 and with this other hand release the locking means by pressing the button 14 with a finger thereof.

Having released the locking mechanism, the operator may keep the distal end of the insertion tube 3 steady in its wedged-in position by maintaining and using the grip of the auxiliary handle 10. At the same time, using the grip of the endoscope handle 2 with the first hand and a thumb on the operating member 8, the operator may bend, turn and advance the bending section 7 further into the alveolus. The bending section 7, in particular the distal end thereof, will largely remain within the range of the camera 12 and thus remain visible on the monitor during this.

The instillation and sampling procedure with suction using the suction button 14 may then be performed as described above, only deeper and more targeted within the alveolus.

Figure 7:
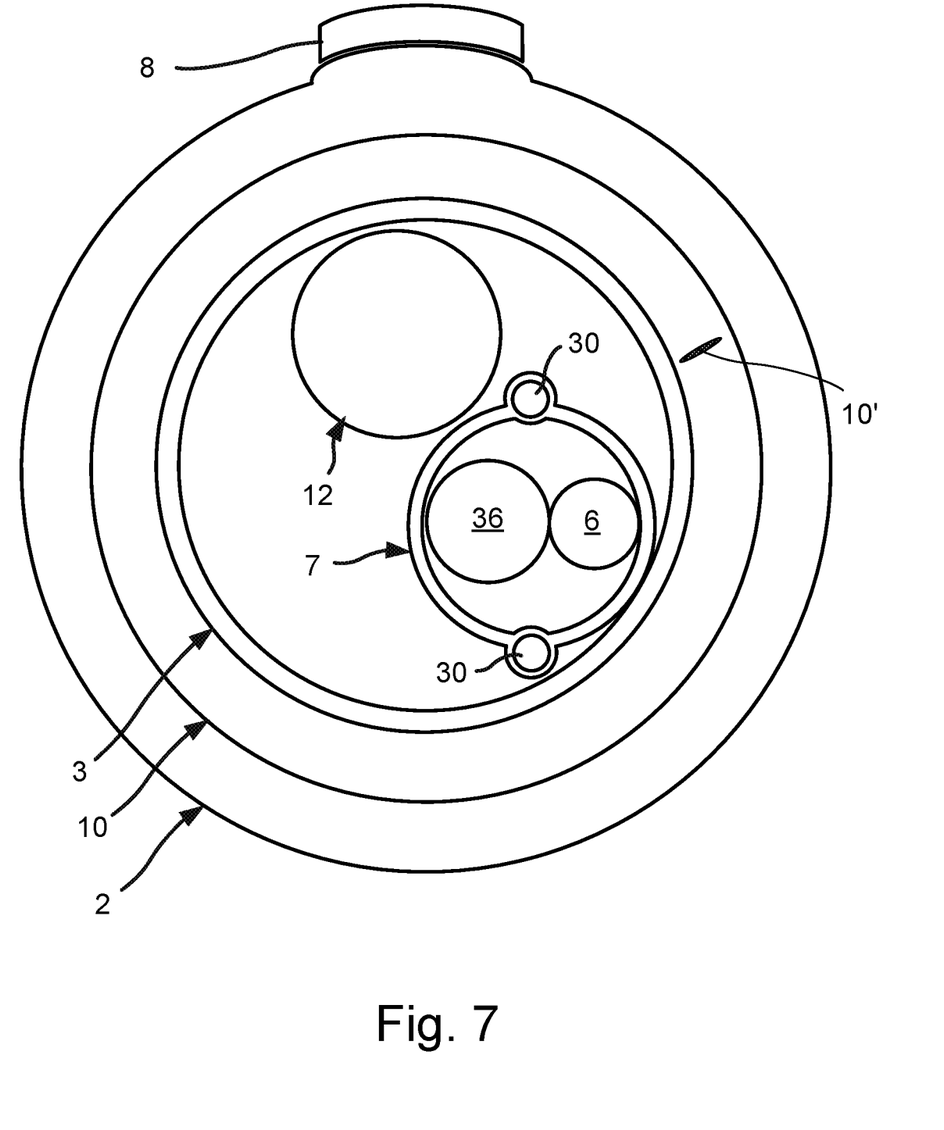
FIG. 7 is a schematic depiction of the front or distal end of another embodiment of an endoscope with the insertion tube rotated clockwise about 50 degrees showing a second camera supported by the bending section of the endoscope.

As an alternative to or in addition to the working channel the distal tip of the bending section 7 could also be provided with a tool. The tool need not necessarily be a complicated tool, but could be a needle, e.g. a biopsy needle. Of course the tool could also be advanced through the working channel in a conventional manner, e.g. as described in the above mentioned documents incorporated by reference. The tool could also be a camera positioned in the most distal segment of the articulated bending section 7, as shown in FIG. 7. Thus, instead of keeping a camera 12 steady at the distal end of the insertion tube 3 the camera may be advanced into the narrower space for inspection. This may also be useful in providing a side view at an angle, to which the distal tip of the insertion tube 3 would not otherwise be bendable, e.g. for providing the above-mentioned inspection of the biliary duct from the duodenum, which would otherwise be complicated because the narrow biliary duct terminates almost perpendicular into the side wall of the duodenum. A camera in both places, as seen in FIG. 7, is of course not excluded.

FIG. 3 is a schematic depiction of the bending section 7 and the insertion tube 3 in a retracted position. The bending section 7 comprises segments including a proximal end segment 20, distal end segment 9, intermediate segments 21 between the proximal end segment 20 and the distal end segment 9, and flexible joints 22 between adjacent segments. The bending section 7 can be molded as a single part. A thin sleeve may be placed over the segments to cover the cutouts between them and seal the bending section 7. The working channel 4 may comprise a tube passing through an insertion shaft 23 connecting the handle 2 to the bending section 7. The distance between the handle 2 and the exit port 6 is substantially constant. The insertion tube 3 slides over the insertion shaft 23 and the bending section 7.

FIG. 4 is a schematic depiction of the bending section 7 and the insertion tube 3 in an extended or locked position of the insertion tube 3. In the locked position the insertion tube 3 extends to the distal end the bending section 7 and the endoscope 1 can be used in a traditional manner.

Figure 5:
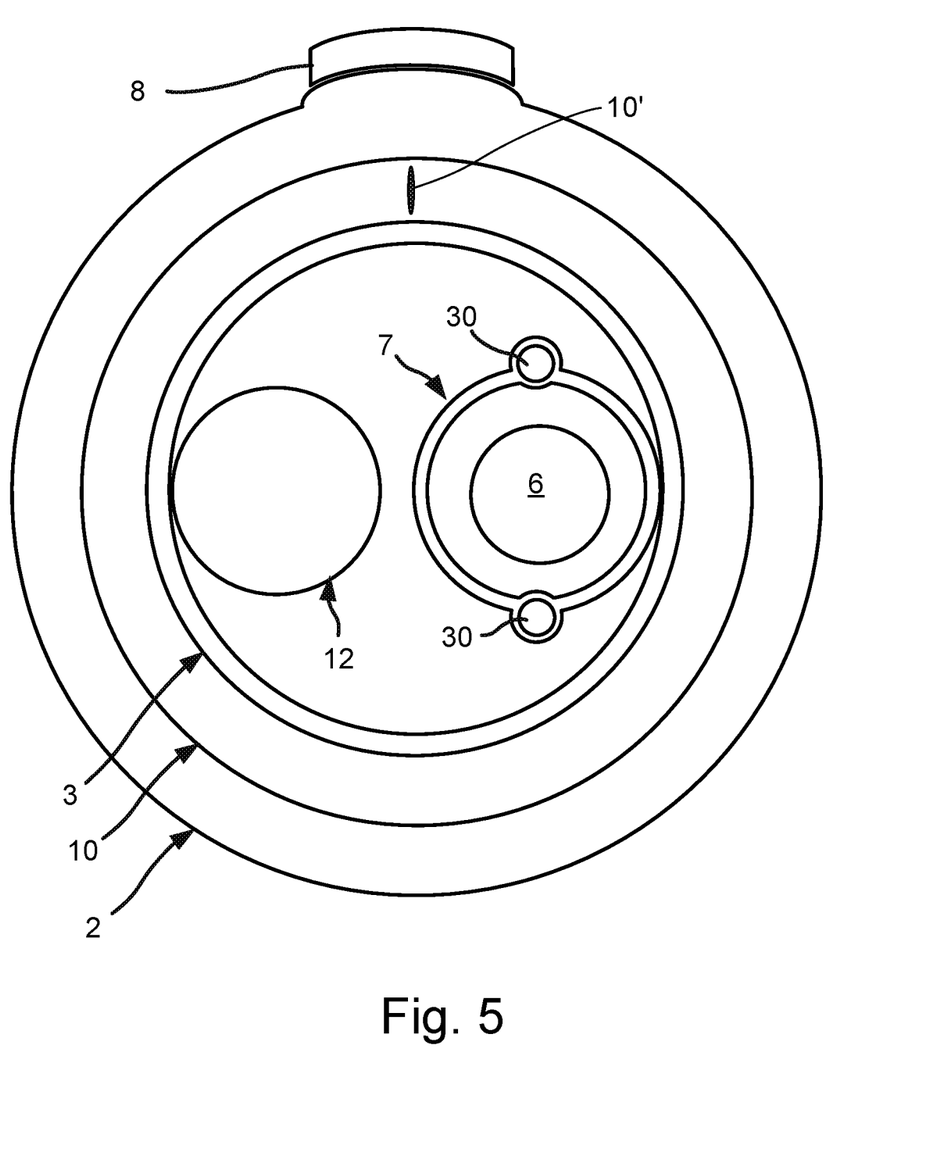
FIG. 5 is a schematic depiction of the front or distal end of the endoscope.

FIG. 5 is a schematic depiction of the front or distal end of the endoscope to illustrate the orientation of the user or articulation control knob 8 in relation to steering wire channels 30 of the bending section 7. The steering wire channels 30 are generally located in a bending plane parallel to a rotation plane of the articulation control knob 8 so that when the user rotates the articulation control knob 8 one wire in one of the steering wire channels 30 is tensioned and the opposite wire is slacked, producing the articulation 7' shown in FIG. 1. Of course, the bending plane can be rotated relative to the rotation plane of the articulation control knob 8. Generally, however, the orientation of the bending plane relative to the rotation plane of the articulation control knob 8 is fixed during manufacturing. The camera 12 is attached to the insertion tube 13 and moves with it. An orientation mark 10' is provided in the auxiliary handle 10 which is aligned with the articulation control knob rotation plane in the locked position. In FIGS. 5-9 a cross-section of the bending section 7 is shown, which is not necessarily the most distal cross-section. The steering wires may be attached to the distal end segment proximally of the most distal cross section.

Figure 6:
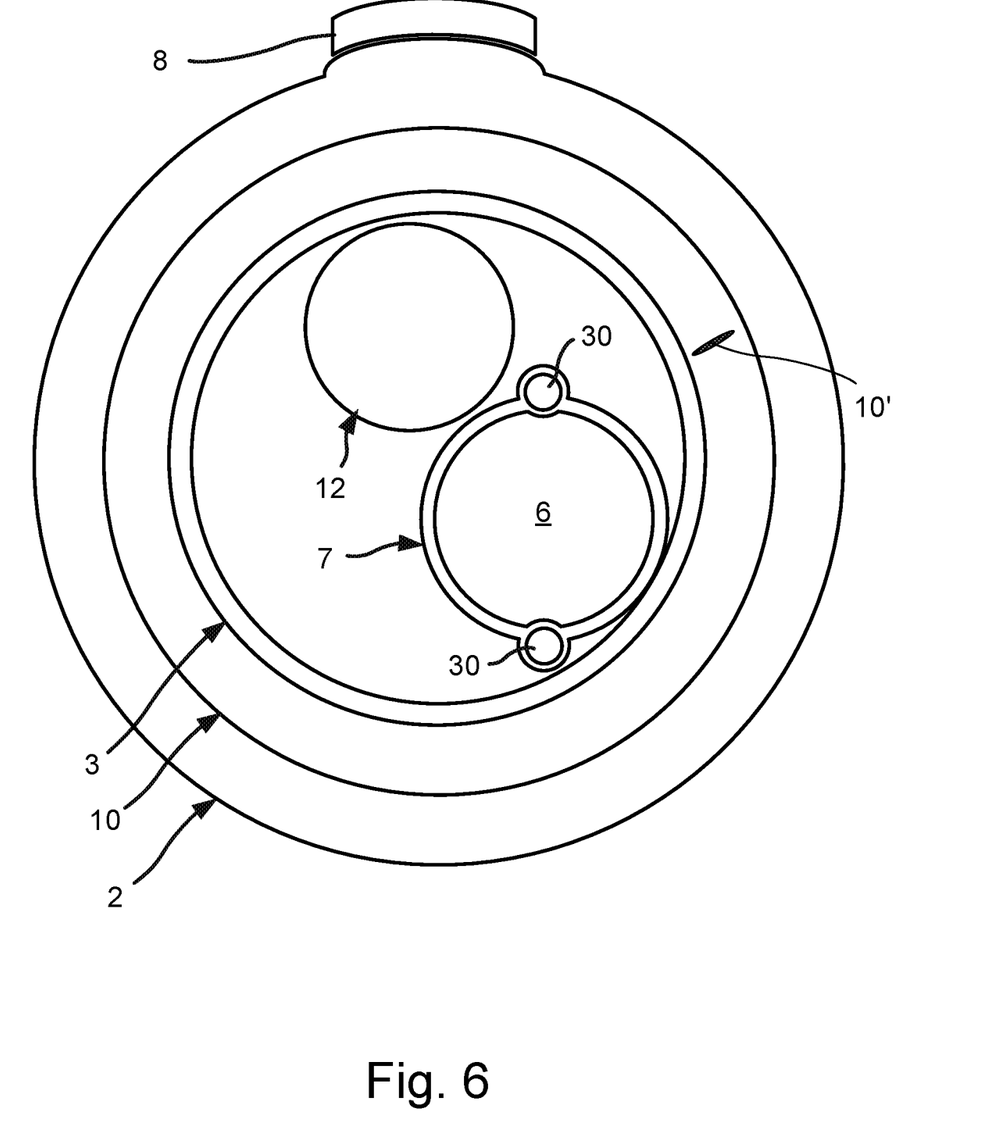
FIG. 6 is a schematic depiction of the front or distal end of the endoscope of FIG. 5 with the insertion tube rotated clockwise about 50 degrees.

FIG. 6 is a schematic depiction of the front or distal end of the endoscope of FIG. 5 with the insertion tube 3 and auxiliary handle 10 rotated clockwise about 50 degrees. It can be seen that the orientation of the bending plane did not change.

FIG. 7 is a schematic depiction of the front or distal end of another embodiment of an endoscope with the insertion tube rotated clockwise about 50 degrees, showing a second camera 36 supported by the bending section 7 of the endoscope.

Figure 8:
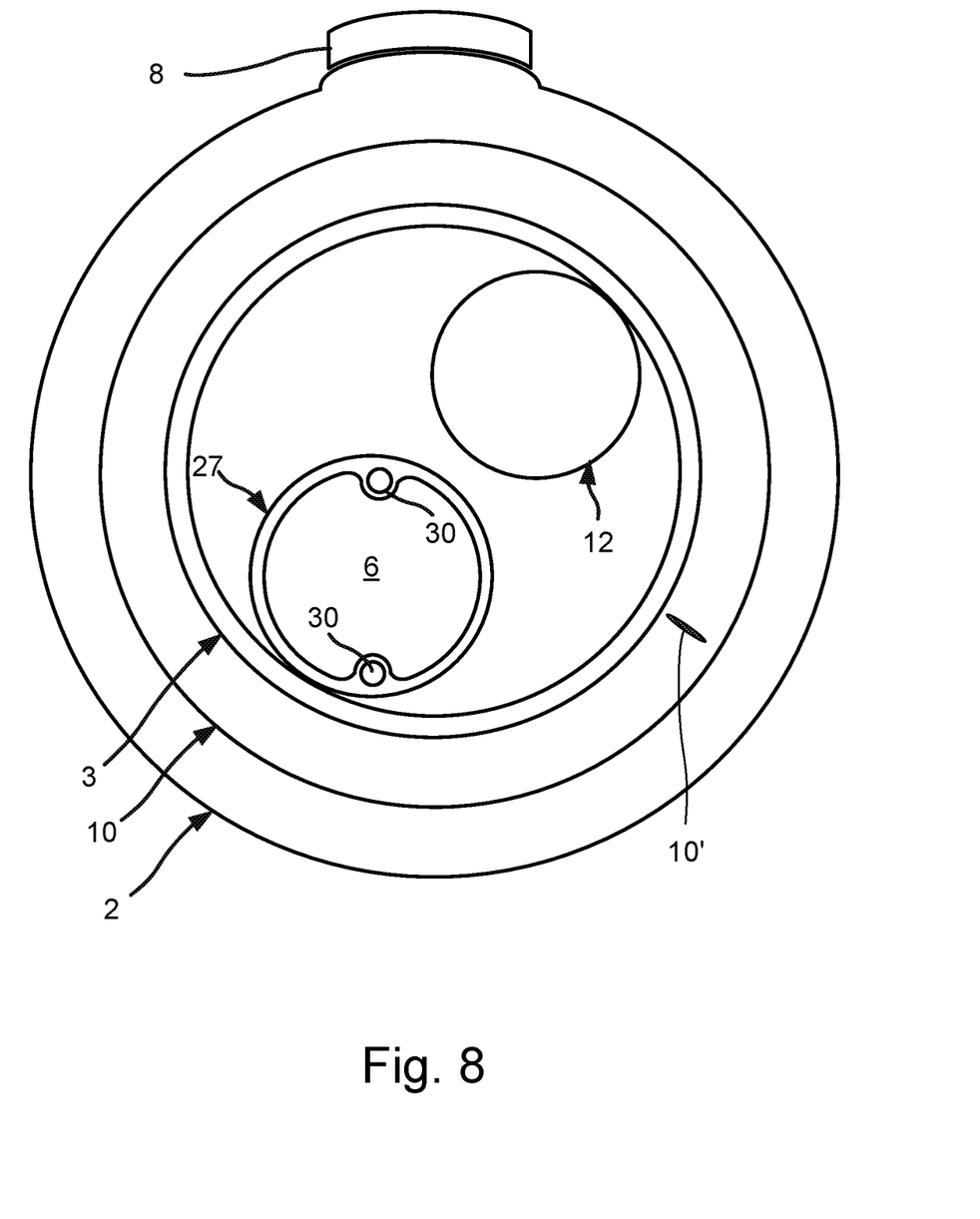
FIG. 8 is a schematic depiction of the front or distal end of yet another embodiment of an endoscope with the insertion tube rotated clockwise more than 90 degrees.

FIG. 8 is a schematic depiction of the front or distal end of yet another embodiment of an endoscope with an insertion tube rotated clockwise more than 90 degrees. The sizes and cross-sectional shapes of the camera(s) and bending sections in part determine the amount of rotation possible. The bending section 27 has the steering wire channels 30 located inside the circular circumferential external surface, which reduces the profile of the bending section but also reduces the amount of space inside the bending section.

Figure 9:
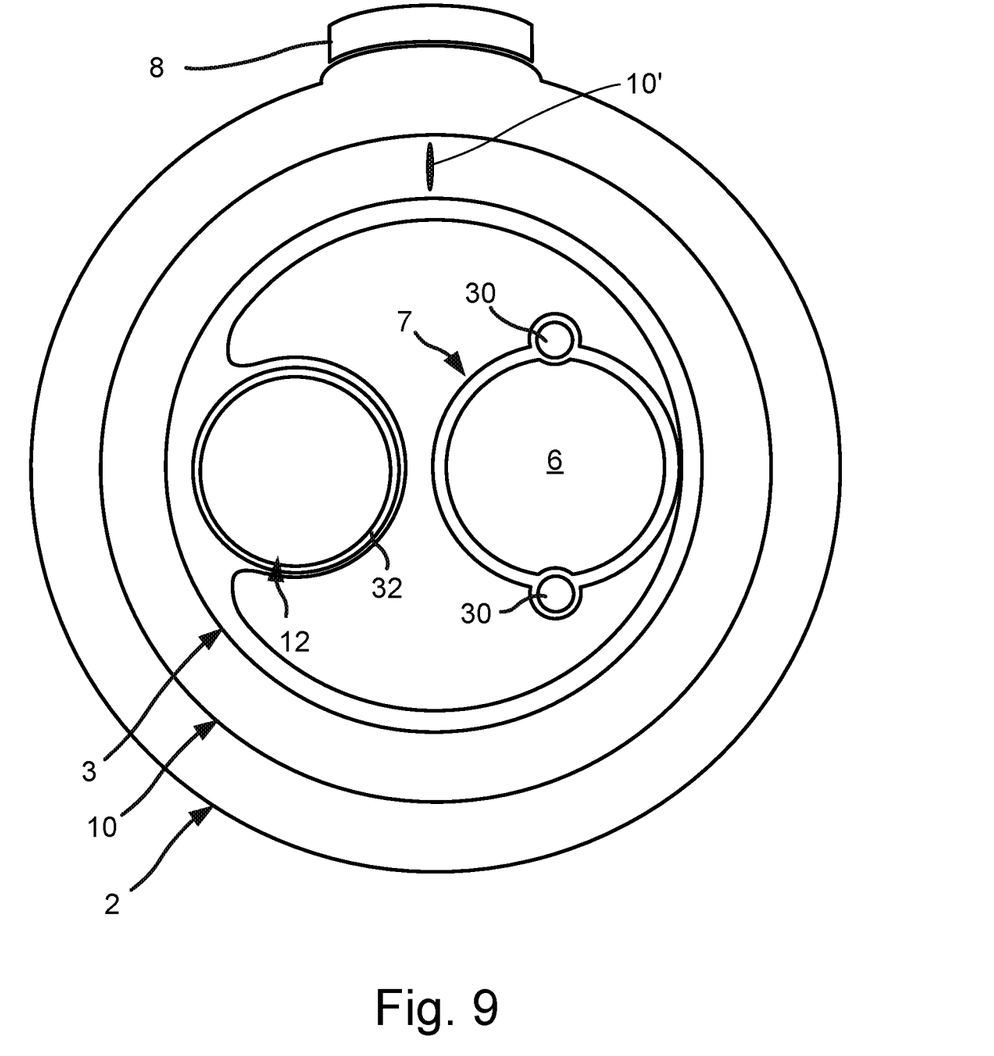
FIG. 9 is a schematic depiction of the front or distal end of yet another embodiment of an endoscope showing a camera lumen in a wall of the insertion tube

FIG. 9 is a schematic depiction of the front or distal end of yet another embodiment of an endoscope showing a camera lumen 32 in a wall of the insertion tube 3. The camera lumen 32 allows insertion of the camera (including the illumination source) therein and passing of a cable including power and signal wires from the camera to the handle 2. The insertion shaft may comprise a slot through which the cable can pass from outside the insertion shaft, between the insertion shaft and the insertion tube, to within the insertion shaft, between the insertion shaft wall and the working channel tube, so that it can then pass to the handle. The cable, or the wires, can include an amount of slack sufficient to permit movement between the insertion shaft and the insertion tube, both radially and longitudinally. Of course, the camera can be attached to the insertion tube in any other way. The camera lumen can be part of any of the insertion tubes described herein in FIGS. 1-8. Similarly, any of the insertion tubes described herein in FIGS. 1-8 can have steering control wires within the circumferential external surface of the bending section.

In embodiments of videoscopes according with the foregoing disclosure, the outer diameter of the bending section 7 may be less than 4 mm, preferably less than 3 mm and may even be less than 2 mm. The outer diameter of the insertion tube 3, on the other and may be less than 7 mm, preferably less than 6 mm and may even be 5 mm or less.

In embodiments of videoscopes according with the foregoing disclosure, the outer diameter of the bending section 7 may be less than 60% of the diameter of the outer diameter of the insertion tube 3, may be 50% or less than the diameter of the outer diameter of the insertion tube 3, and may even be less than 40%.

Figure 10:
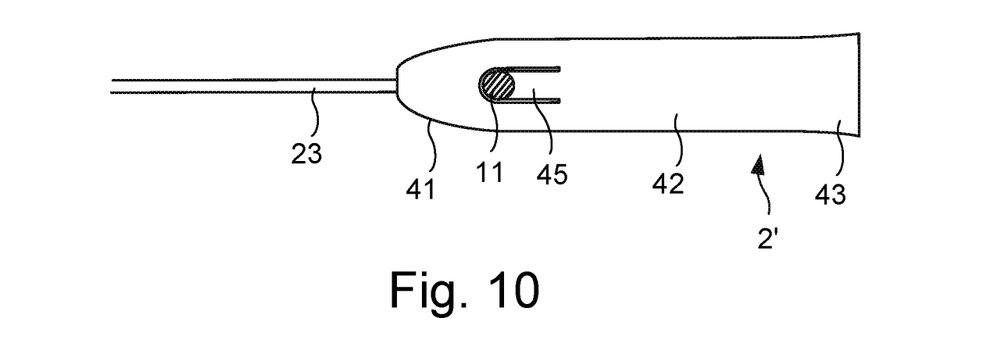
FIG. 10 is a schematic depiction of an embodiment of a distal portion of the handle.

FIG. 10 is a schematic depiction of an embodiment of a distal portion of the handle which may be referred to as a handle extension 2'. Handle extension 2' extends from a body a handle and its function is to mate with the auxiliary handle 10. As shown, handle extension 2' has a distal portion 41 connected to the insertion shaft 23, an intermediate portion 42, and a proximal portion 43. The intermediate portion 42 may comprise a circular cross-section to facilitate rotation of the auxiliary handle 10. A tab 45 is formed by a U-shaped slot. At the distal end the tab 45 has button 11. The tab permits button 11 to recede inwardly to unlock the auxiliary handle 10. Proximal portion 43 is flared to create a friction fit with the auxiliary handle 10 when it is retracted.

Figure 11:
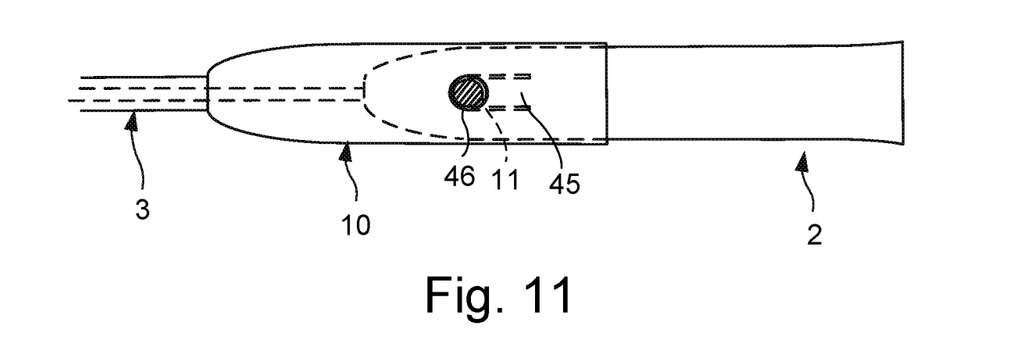
FIG. 11 is a schematic depiction of the insertion tube and auxiliary handle in the locked position.
Figure 12:
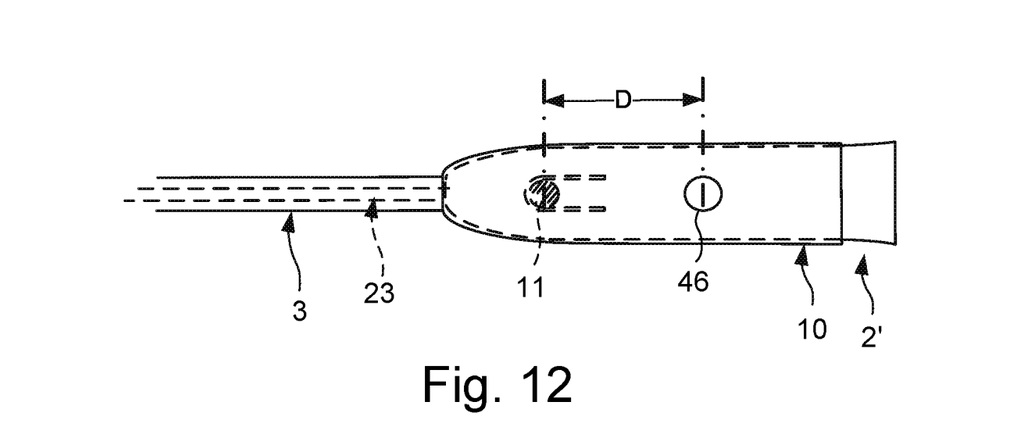
FIG. 12 is a schematic depiction of the auxiliary handle in the retracted position.

FIG. 11 is a schematic depiction of the auxiliary handle 10 in the locked position. An aperture 46 on the auxiliary handle 10 receives button 11 and the periphery of button 11 prevents longitudinal movement of the auxiliary handle 10. When the user moves the button inwardly, below the internal surface of the wall of the auxiliary handle 10, the auxiliary handle 10 can be slid proximally to the retracted position as shown in FIG. 12. The distance D between the button 11 and the aperture 46 is indicative of the amount of longitudinal translation of the bending section 7 and is a predetermined protrusion length. In some examples, the predetermined protrusion length comprises at least 70% of the bending section 7, and preferably at least 80%.

The following additional embodiments expand and further exemplify the features described above:

An videoscope comprising a handle arranged at a proximal end, an insertion tube extending from said handle towards a distal end, a controllable bending section arranged at the distal end, said controllable bending section being controllable by and operator via control input means arranged at the handle, wherein the insertion tube comprises at least one insertion tube part with at least one lumen and wherein the bending section is displaceable in said lumen so as to be movable relative to the insertion tube part from a retracted position within said lumen to an extended position at least partially outside said lumen, and wherein the controllable bending section is located at a fixed distance from the handle, and the at least one insertion tube part is adapted for a reciprocating movement with respect to the handle.

A videoscope according to embodiment 1, wherein the at least one insertion tube part is adapted for a releasable locking engagement with respect to the handle.

A videoscope according to embodiment 1 or 2, wherein the controllable bending section comprises a number of articulated parts.

A videoscope according to any one of the preceding embodiments, wherein the at least one insertion tube part comprises a vision device.

A videoscope according to embodiment 4, wherein the vision device comprises a camera.

A videoscope according to any one of the preceding embodiments, wherein the controllable bending section comprises a working channel.

A videoscope according to embodiment 6, wherein the working channel is adapted for suction.

A videoscope according to any one of the preceding embodiments, wherein the controllable bending section comprises a tool.

A videoscope according to any one of the preceding embodiments wherein the tool comprises a needle.

The invention claimed is:

1. An endoscope comprising:
a handle including a steering control knob;
an insertion shaft affixed to the handle;
a bending section affixed to the insertion shaft at a fixed distance from the handle, the bending section being sized and shaped to bend along a bending plane; and
an insertion tube extending from the handle, the insertion tube including a lumen and being sized and shaped to translate longitudinally relative to the handle from a locked position to a retracted position,
a vision device located, at least in part, between an outer circumferential surface of the bending section and an inner circumferential surface of the insertion tube, the vision device supported by the insertion tube to translate therewith,
wherein a portion of the bending section is positioned within the lumen in the locked position, and
wherein the portion of the bending section is positioned outside the lumen in the retracted position.

2. The endoscope of claim 1, further comprising a button depressable to release the insertion tube from the locked position.

3. The endoscope of claim 1, wherein the vision device comprises a camera positioned at a distal end of the insertion tube.

4. The endoscope of claim 3, further comprising a camera supported by the bending section.

5. The endoscope of claim 1, wherein the bending section comprises a single piece including segments connected by flexible joints.

6. The endoscope of claim 5, further comprising a camera supported by the bending section.

7. The endoscope of claim 1, further comprising a working channel extending from the handle to a distal end of the bending section.

8. The endoscope of claim 1, further comprising a tool supported by the bending section.

9. The endoscope of claim 8, wherein the tool comprises a needle.

10. An endoscope comprising:
a handle including a steering control knob;
an insertion shaft affixed to the handle;
a bending section affixed to the insertion shaft at a fixed distance from the handle, the bending section being sized and shaped to bend along a bending plane;
an insertion tube extending from the handle, the insertion tube including a lumen and being sized and shaped to translate longitudinally relative to the handle from a locked position to a retracted position, wherein a portion of the bending section is positioned within the lumen in the locked position, and wherein the portion of the bending section is positioned outside the lumen in the retracted position;
releasable locking means operable to place the insertion tube in the locked position and to release the insertion tube from the locked position; and an auxiliary handle affixed to the insertion tube and sized and shaped to translate over a distal end of the handle to place the insertion tube in the locked position.

11. A method of using an endoscope, comprising:
gripping an endoscope including:
a handle including a steering control knob;
an insertion shaft affixed to the handle;
a bending section affixed to the insertion shaft at a fixed distance from the handle, the bending section being sized and shaped to bend along a bending plane;
an insertion tube extending from the handle, the insertion tube including a lumen and being sized and shaped to translate longitudinally relative to the handle from a locked position to a retracted position; and
a vision device located, at least in part, between an outer circumferential surface of the bending section and an inner circumferential surface of the insertion tube, the vision device supported by the insertion tube to translate therewith,
wherein a portion of the bending section is positioned within the lumen in the locked position, and
wherein the portion of the bending section is positioned outside the lumen in the retracted position;
with the insertion tube in the locked position, inserting the insertion tube into a patient;
causing a distal end of the insertion tube to contact tissue of the patient;
releasing the insertion tube from the locked position;
retracting the insertion tube; and
after retracting the insertion tube, steering the bending section.

12. The method of claim 11, further comprising, after retracting the insertion tube, obtaining a sample.

13. The method of claim 12, wherein obtaining a sample comprises obtaining a tissue sample with a needle supported by the bending section.

14. The method of claim 12, wherein obtaining a sample comprises flushing a volume distal of the bending section with a liquid and suctioning the liquid.

15. A videoscope comprising:
a handle including a handle extension;
an auxiliary handle sized and shaped to translate and rotate on the handle extension;
an insertion tube affixed to the auxiliary handle and including a lumen, the insertion tube sized and shaped to translate longitudinally relative to the handle from a locked position to a retracted position;
a vision device located, at least in part, between an outer circumferential surface of the bending section and an inner circumferential surface of the insertion tube, the vision device supported by the insertion tube to translate therewith;
an insertion shaft having a proximal end affixed to the handle extension and a distal end, the insertion shaft positioned within the lumen; and
a bending section affixed to the distal end of the insertion shaft at a fixed distance from the handle,
wherein a portion of the bending section is positioned within the lumen in the locked position, and
wherein the portion of the bending section is positioned outside the lumen in the retracted position.

16. The videoscope of claim 15, further comprising releasable locking means operable to place the insertion tube in the locked position and to release the insertion tube from the locked position.

17. The videoscope of claim 16, wherein the releasable locking means includes a tab in the handle extension, the tab being flexible, an opening in the auxiliary handle, and a button protruding from the tab through the opening in the locked position, wherein pressing the button enables a user to move the handle extension relative to the auxiliary handle.

18. The videoscope of claim 15, wherein an outer diameter of the bending section is less than 60% of an outer diameter of the insertion tube.

19. The videoscope of claim 18, wherein the vision device comprises a camera.

20. The videoscope of claim 18, wherein the outer diameter of the bending section is 3 mm or less.

* * * * *